US00PP32116P3

(12) United States Plant Patent
Schoemaker

(10) Patent No.: US PP32,116 P3
(45) Date of Patent: Aug. 25, 2020

(54) ***HYDRANGEA* PLANT NAMED 'LC NO2'**

(50) Latin Name: *Hydrangea paniculata*
Varietal Denomination: LC NO2

(71) Applicant: Alex Frederick Schoemaker, Boskoop (NL)

(72) Inventor: Alex Frederick Schoemaker, Boskoop (NL)

( * ) Notice: Subject to any disclaimer, the term of this patent is extended or adjusted under 35 U.S.C. 154(b) by 0 days.

(21) Appl. No.: 16/602,287

(22) Filed: Sep. 6, 2019

(65) Prior Publication Data

US 2020/0084945 P1 Mar. 12, 2020

Related U.S. Application Data

(60) Provisional application No. 62/765,663, filed on Sep. 7, 2018.

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/02; A01H 6/48
See application file for complete search history.

(56) References Cited

PUBLICATIONS

Pluto Plant Variety Database Mar. 3, 2020. p. 1.*

* cited by examiner

*Primary Examiner* — Annette H Para
(74) *Attorney, Agent, or Firm* — C. A. Whealy

(57) ABSTRACT

A new and distinct cultivar of *Hydrangea* plant named 'LC NO2', characterized by its medium size and upright to broadly upright plant habit; moderately freely branching habit with strong lateral branches; freely flowering habit with plants remaining in flower for a long period time; dense and hardy inflorescences with white-colored sterile flowers that age attractively to greyed purple in color with development; and good garden performance.

3 Drawing Sheets

Figure 1:
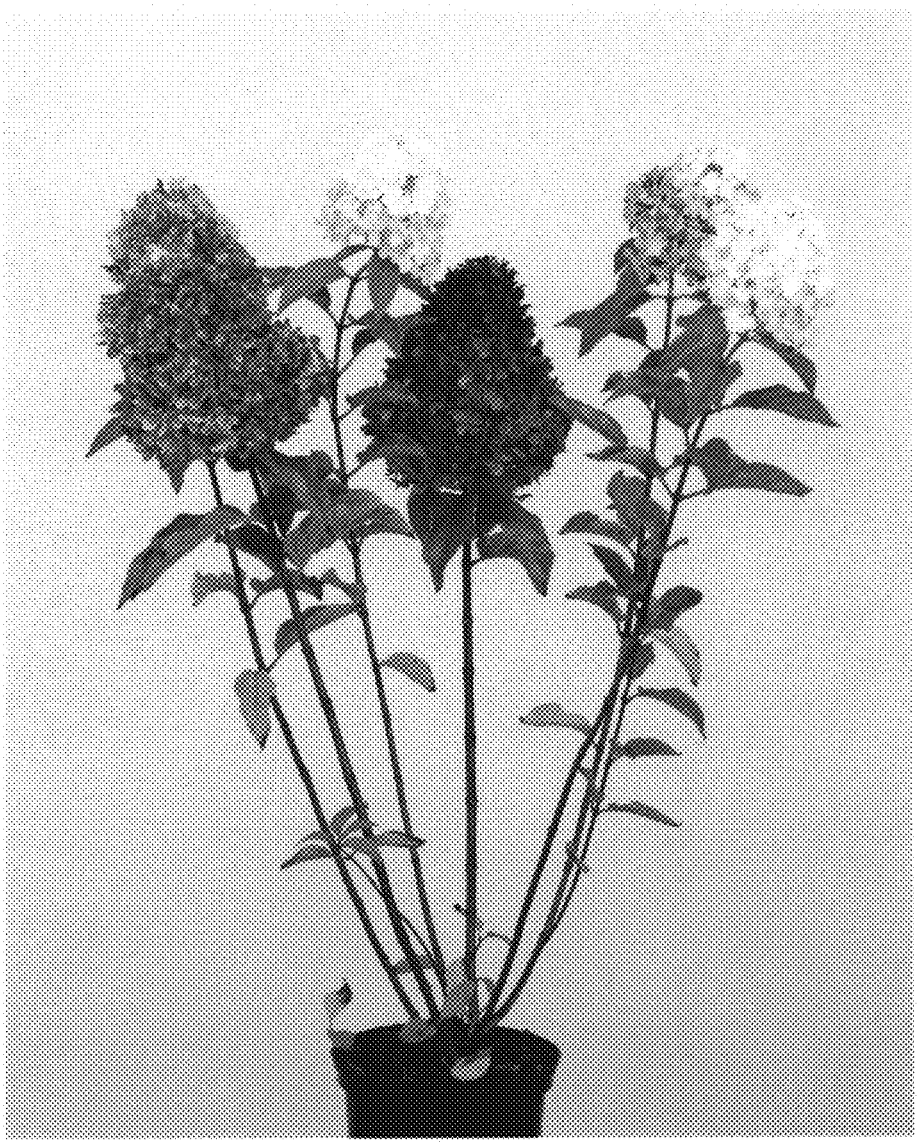

Botanical designation: *Hydrangea paniculata.*
Cultivar denomination: 'LC NO2'.

CROSS-REFERENCED TO CLOSELY RELATED APPLICATIONS

Title: Varieties of *Hydrangea* Plants
Applicant: Alex Frederick Schoemaker
Provisional application Ser. No. 62/765,663
Filed: Sep. 7, 2018
Title: *Hydrangea* Plant Named 'LC NO5'
Applicant: Alex Frederick Schoemaker
Filed: Plant patent application Ser. No. 16/602,282
Title: *Hydrangea* Plant Named 'LC NO7'
Applicant: Alex Frederick Schoemaker
Filed: Plant patent application Ser. No. 16/602,283

BACKGROUND OF THE INVENTION

The present invention relates to a new and distinct cultivar of *Hydrangea* plant, botanically known as *Hydrangea paniculata*, commercially referred to as a Hardy or Panicled *Hydrangea* and hereinafter referred to by the name 'LC NO2'.

The new *Hydrangea* plant is a product of a planned breeding program conducted by the Inventor in Boskoop, The Netherlands. The objective of the breeding program is to create new *Hydrangea* plants with uniform plant habit and attractive inflorescences.

The new *Hydrangea* plant originated from an open-pollination in July, 2011 in Boskoop, The Netherlands, of *Hydrangea paniculata* 'Limelight', disclosed in U.S. Plant Pat. No. 12,874, as the female, or seed, parent with an unknown selection of *Hydrangea paniculata* as the male, or pollen, parent. The new *Hydrangea* plant was discovered and selected by the Inventor as a single flowering plant from within the progeny of the stated open-pollination in a controlled greenhouse environment in Boskoop, The Netherlands during the summer of 2016.

Asexual reproduction of the new *Hydrangea* plant by vegetative tip cuttings in a controlled environment in Boskoop, The Netherlands since the summer of 2016 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'LC NO2'. These characteristics in combination distinguish 'LC NO2' as a new and distinct *Hydrangea* plant:

1. Medium in size and upright to broadly upright plant habit.
2. Moderately freely branching habit with strong lateral branches.
3. Freely flowering habit with plants remaining in flower for a long period time.
4. Dense and hardy inflorescences with white-colored sterile flowers that age attractively to greyed purple in color with development.
5. Good garden performance.

Plants of the new *Hydrangea* can be compared to plants of the female parent, 'Limelight'. Plants of the new *Hydrangea* differ primarily from plants of 'Limelight' in the following characteristics:

1. Plants of the new *Hydrangea* are more compact than plants of 'Limelight'.
2. Plants of the new *Hydrangea* and 'Limelight' differ in sterile flower color as sterile flowers of plants of the new *Hydrangea* are white in color becoming greyed purple in color with development whereas sterile flowers of plants of 'Limelight' are light green in color and maintain this color with development.

Plants of the new *Hydrangea* can be compared to plants of the *Hydrangea paniculata* 'LC NO5', disclosed in a U.S. Plant patent application Ser. No. 16/602,282. In side-by-side comparisons, plants of the new *Hydrangea* differ primarily from plants of 'LC NO5' in plant habit as plants of the new *Hydrangea* are taller and broader and narrower than plants of 'LC NO5'.

Plants of the new *Hydrangea* can be compared to plants of the *Hydrangea paniculata* 'LC NO7', disclosed in a U.S. Plant patent application Ser. No. 16/602,283. In side-by-side comparisons, plants of the new *Hydrangea* differ primarily from plants of 'LC NO7' in plant habit as plants of the new *Hydrangea* are shorter and narrower than plants of 'LC NO7'. In addition, plants of the new *Hydrangea* are not as freely branching as plants of 'LC NO7'.

Plants of the new *Hydrangea* can also be compared to plants of the *Hydrangea paniculata* 'Silver Dollar', not patented. In side-by-side comparisons, plants of the new *Hydrangea* differ primarily from plants of 'Silver Dollar' in the following characteristics:

1. Inflorescences of plants of the new *Hydrangea* are denser than and not as open as inflorescences of plants of 'Silver Dollar'.
2. Plants of the new *Hydrangea* and 'Silver Dollar' differ in sterile flower color as sterile flowers of plants of the new *Hydrangea* white in color becoming greyed purple in color with development whereas sterile flowers of plants of 'Silver Dollar' are white in color and maintain this color with development.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1 of 3) is a side perspective view of a typical flowering plant of 'LC NO2'.

Figure 2:
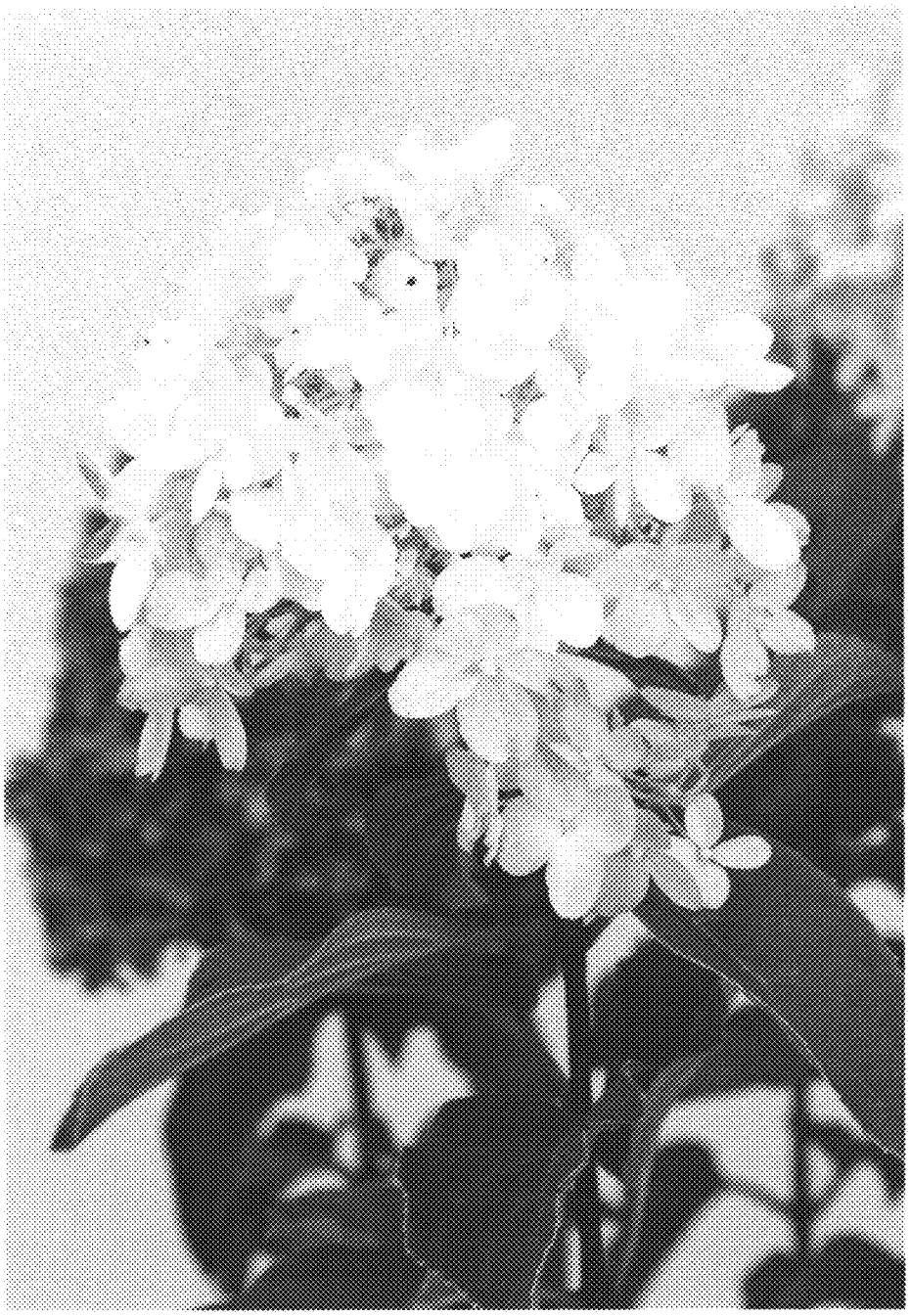

The photograph on the second sheet (FIG. 2 of 3) is a close-up view of typical inflorescences of 'LC NO2'.

Figure 3:
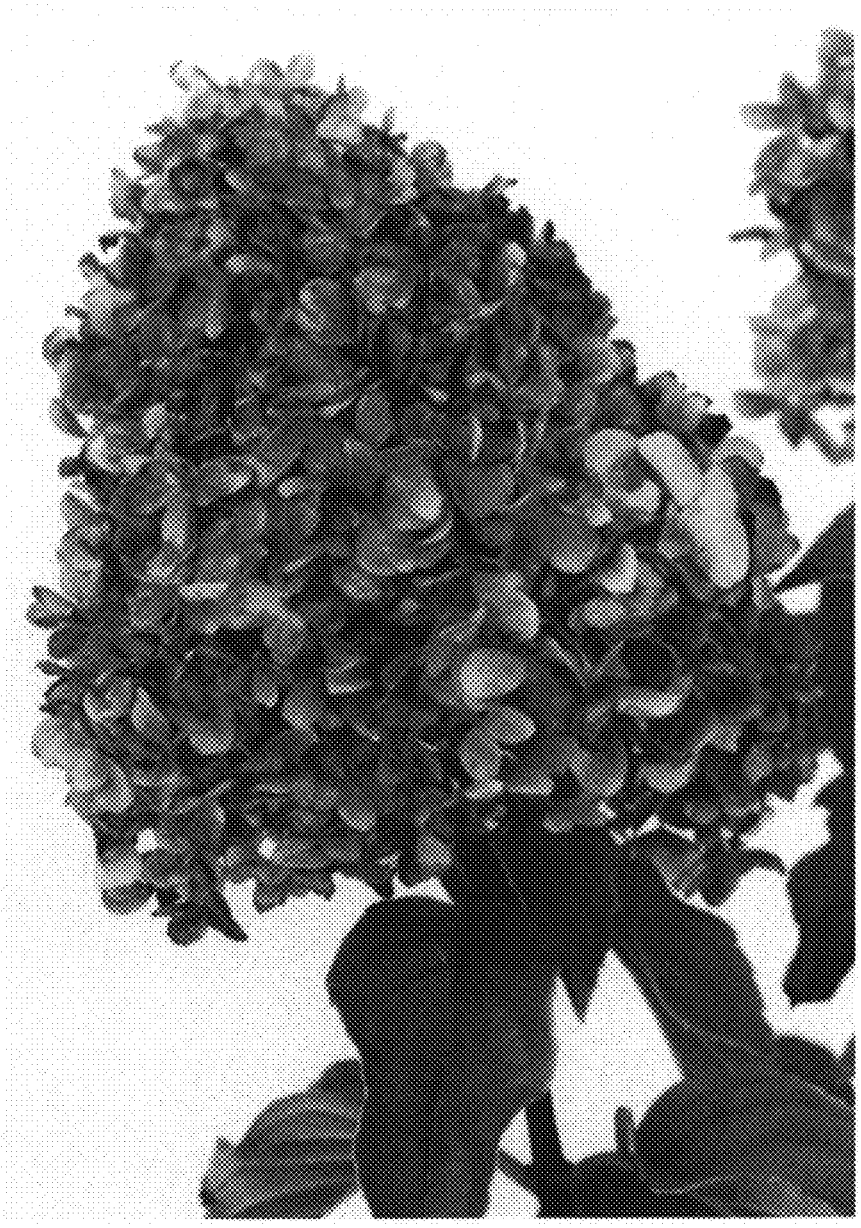

The photograph on the third sheet (FIG. 3 of 3) is a close-up view of typical inflorescence of 'LC NO2' with subsequent development.

DETAILED BOTANICAL DESCRIPTION

Plants used in the aforementioned photographs and in the following description were grown during the late summer in 15-cm containers in an outdoor nursery in Boskoop, The Netherlands and under cultural practices typical of commercial *Hydrangea* production. During the production of the plants, day temperatures ranged from about 16° C. to 25° C. and night temperatures ranged from about averaged 5° C. to 16° C. Plants of the new *Hydrangea* were pinched one time and were two years old when the photographs and description were taken. As a Hardy or Panicled *Hydrangea*, plants of the new *Hydrangea* are typically not treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea paniculata* 'LC NO2'.

Parentage:

*Female, or seed, parent.*—*Hydrangea paniculata* 'Limelight', disclosed in U.S. Plant Pat. No. 12,874.

*Male, or pollen, parent.*—Unknown selection of *Hydrangea paniculata*, not patented.

Propagation:

*Type cutting.*—By vegetative tip cuttings.

*Time to initiate roots, summer.*—About 20 days at temperatures about 16° C. to 30° C.

*Time to produce a rooted young plant, summer.*—About 50 days at temperatures about 16° C. to 30° C.

*Root description.*—Medium in thickness, fibrous; typically light brown in color, actual color of the roots is dependent on substrate composition, water quality, fertilizer type and formulation, substrate temperature and physiological age of roots.

*Rooting habit.*—Freely branching; dense.

Plant description:

*Plant and growth habit.*—Medium-sized, upright to broadly upright plant habit; overall plant shape, narrowly obovate; strong and sturdy stems; moderately vigorous to vigorous growth habit and moderate to rapid growth rate.

*Plant height.*—About 68.5 cm.

*Plant diameter or area of spread.*—About 50.5 cm.

Lateral branch description:

*Branching habit.*—About seven lateral branches develop per plant; pinching will enhance lateral branch development.

*Length.*—About 50.1 cm.

*Diameter.*—About 5 mm.

*Internode length.*—About 4.5 cm.

*Texture.*—When developing, smooth, glabrous; fully developed, woody.

*Aspect.*—Upright to about 30° from vertical.

*Strength.*—Strong, sturdy.

*Color.*—When developing: Close to 195B to 195C. Developed: Close to 200D; when woody, close to 199C, 199D and 200D.

*Lenticels.*—Density: Sparse to medium density. Size: About 1.5 mm by 0.75 mm. Color, developing stems: Close to N170D. Color, developed stems: Close to 177D.

Leaf description:

*Arrangement.*—Opposite, simple.

*Length.*—About 8.3 cm.

*Width.*—About 4.4 cm.

*Shape.*—Ovate to elliptic.

*Apex.*—Apiculate.

*Base.*—Obtuse.

*Margin.*—Serrate.

*Texture, upper and lower surfaces.*—Smooth, glabrous; venation moderately pubescent; slightly rugose.

*Venation pattern.*—Pinnate.

*Color.*—Developing leaves, upper surface: Close to 144A to 144B. Developing leaves, lower surface: Close to 145A. Fully developed leaves, upper surface: Close to between 143B and 144A; venation, close to 147C. Fully developed leaves, lower surface: Close to 144B; venation, close to 179D.

*Petioles.*—Length: About 1.6 cm. Diameter: About 2.5 mm. Texture, upper surface: Smooth, glabrous; margins, sparsely pubescent. Texture, lower surface: Sparsely pubescent. Color, upper surface: Close to 180A to 180B. Color, lower surface: Close to 179C to 179D.

Flower description:

*Flower type and habit.*—Showy sterile flowers and small inconspicuous fertile flowers arranged on terminal panicles; panicles broadly conical in shape; sterile flowers face upright to outwardly and slightly drooping depending on their position in the inflorescence; fertile flowers face mostly upright.

*Fragrance.*—Faintly fragrant; sweet and pleasant.

*Natural flowering season.*—Flowering begins in the midsummer and is continuous until late summer in Northern Europe.

*Flower longevity.*—Sterile flowers last about six weeks on the plant, sterile flowers persistent; fertile flowers last about five days on the plant, fertile flowers not persistent.

*Quantity of flowers.*—Freely flowering habit; about 600 sterile flowers and about 700 fertile flowers per panicle.

*Panicle height.*—About 15.8 cm.

*Panicle diameter.*—About 14.4 cm.

*Sterile flower buds.*—Length: About 6 mm. Diameter: About 8 mm. Shape: Cup-shaped. Color: Close to 155C.

*Fertile flower buds.*—Length: About 3 mm. Diameter: About 2 mm. Shape: Obovate. Color: Close to 155C; towards the margins, close to 180D; immature calyx, close to 157D.

*Sterile flower diameter.*—About 2.9 cm.

*Sterile flower depth (height).*—About 5 mm.

*Fertile flower diameter.*—About 1 cm.

*Fertile flower depth (height).*—About 7 mm.

*Petals, sterile flowers.*—Quantity and arrangement: Four in a single whorl. Length: About 2 mm. Width: About 1.5 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to NN155D; color does not change with development. When opening and fully opened, lower surface: Close to NN155D; color does not change with development.

*Petals, fertile flowers.*—Quantity and arrangement: Five in a single whorl. Length: About 3 mm. Width: About 2 mm. Shape: Ovate, concave. Apex: Acute. Base: Cuneate. Margin: Entire. Texture and luster, upper and lower surfaces: Smooth, glabrous; slightly glossy. Color: When opening and fully opened, upper surface: Close to NN155C; color does not change with development. When opening and fully opened, lower surface: Close to NN155C; color does not change with development.

*Sepals, sterile flowers.*—Quantity and arrangement: Typically four in a single whorl. Length: About 1.5 cm. Width: About 1.1 cm. Shape: Ovate to elliptic. Apex: Obtuse. Base: Cuneate. Margin: Entire. Texture and luster, upper and lower surfaces: Smooth, glabrous; matte. Color: When opening, upper surface: Close to 155B. When opening, lower surface: Close to 155C. Fully opened, upper surface: Close to between 155A and 157D; color becoming closer to 184D with subsequent development. Fully opened, lower surface: Close to 155A; color becoming closer to 185D with subsequent development.

*Sepals, fertile flowers.*—Quantity and arrangement: Five in a single whorl. Length: About 1 mm. Width: About 1.25 mm. Shape: Close to deltoid. Apex: Broadly acuminate. Base: Broadly cuneate. Margin: Entire. Texture and luster, upper and lower surfaces: Smooth, glabrous; matte. Color: When opening and fully opened, upper surface: Close to 157C to 157D; color does not change with development. When opening and fully opened, lower surface: Close to 157C to 157D; color does not change with development.

*Pedicels, sterile flowers.*—Length: About 1.5 cm. Diameter: About 0.8 mm. Strength: Moderately strong. Aspect: About 55° from branch axis. Texture and luster: Moderately pubescent; matte. Color: Close to 155C.

*Pedicels, fertile flowers.*—Length: About 2.5 mm. Diameter: About 0.5 mm. Strength: Moderately strong. Aspect: About 20° from vertical. Texture and luster: Moderately pubescent; matte. Color: Close to 155C.

*Reproductive organs, sterile flowers.*—Stamens: Quantity per flower: About eight. Filament length: About 3 mm. Filament color: Close to NN155D. Anther length: About 0.5 mm. Anther shape: Broadly oblong. Anther color: Close to 155C. Pollen amount: Moderate. Pollen color: Close to 156A. Pistils: To date, pistil development on sterile flowers of the new *Hydrangea* has not been observed.

*Reproductive organs, fertile flowers.*—Stamens: Quantity per flower: About ten. Filament length: About 5 mm. Filament color: Close to NN155D. Anther length: About 0.5 mm. Anther shape: Broadly oblong. Anther color: Close to 155C. Pollen amount: Moderate. Pollen color: Close to 156A. Pistils: Pistil quantity per flower: Typically three. Pistil length: About 1 mm. Stigma shape: Club-shaped. Stigma color: Close to 155A. Style length: About 0.5 mm. Style color: Close to 157D. Ovary color: Close to 157D.

*Seeds.*—To date, seed production has not been observed on plants of the new *Hydrangea*.

Pathogen & pest resistance: To date, under commercial production conditions, plants of the new *Hydrangea* have not been observed to be resistant to pathogens and pests common to *Hydrangea* plants.

Garden performance: Plants of the new *Hydrangea* have been observed have good garden performance and to be suitable for USDA Hardiness Zones 5 through 9.

It is claimed:

1. A new and distinct *Hydrangea* plant named 'LC NO2' as illustrated and described.

* * * * *